United States Patent

Zdeb

[11] Patent Number: 5,135,500
[45] Date of Patent: Aug. 4, 1992

[54] SELF-DRIVEN PUMP DEVICE

[75] Inventor: Brian D. Zdeb, Round Lake Park, Ill.

[73] Assignee: Prime Medical Products, Inc., Round Lake Park, Ill.

[21] Appl. No.: 429,412

[22] Filed: Oct. 31, 1989

[51] Int. Cl.⁵ .............................................. A61M 5/00
[52] U.S. Cl. ...................................... 604/143; 604/131; 604/141
[58] Field of Search ............... 604/131, 140, 141, 143, 604/151; 222/386, 387, 389

[56] References Cited

U.S. PATENT DOCUMENTS

| | | | |
|---|---|---|---|
| 921,130 | 5/1909 | Lockwood | 604/141 |
| 1,105,275 | 7/1914 | Ingalls | 604/143 |
| 1,471,091 | 10/1923 | Bessesen | 604/141 X |
| 1,541,615 | 6/1925 | Bessesen | 604/143 |
| 2,545,017 | 3/1951 | Billingsley | 604/143 |
| 2,582,112 | 1/1952 | Ferguson | 222/389 X |
| 3,604,417 | 9/1971 | Stolzenberg | 604/143 X |
| 3,850,348 | 11/1974 | Bessot et al. | 604/141 X |
| 3,917,124 | 11/1975 | Kifer | 222/386 |
| 4,085,749 | 4/1978 | Chambron | 604/143 |
| 4,089,334 | 5/1978 | Schwebel et al. | 604/143 X |
| 4,124,024 | 11/1978 | Schwebel et al. | 604/140 X |
| 4,326,650 | 4/1982 | Van Manen | 222/386 |
| 4,447,231 | 5/1984 | Bekkering | 604/131 |
| 4,636,197 | 1/1987 | Chu | 604/131 |
| 4,861,340 | 8/1989 | Smith et al. | 604/141 |
| 4,969,874 | 11/1990 | Michel et al. | 604/140 |
| 4,969,884 | 11/1990 | Yum | 604/141 X |

Primary Examiner—Richard J. Apley
Assistant Examiner—Linda C. M. Dorak
Attorney, Agent, or Firm—Leydig, Voit & Mayer

[57] ABSTRACT

An apparatus for delivering fluid with a relatively constant, controlled rate of flow comprises a vacuum power means, a fluid storage means in axial alignment with the vacuum power means and a plunger means carried by the vacuum power means and in axial communication with the fluid storage means. The plunger means is driven by a vacuum which collapses under atmospheric pressure, and as it is driven it effects delivery of the fluid from the fluid storage means.

25 Claims, 5 Drawing Sheets

SELF-DRIVEN PUMP DEVICE

BACKGROUND OF THE INVENTION

1. Field of the Invention

This invention relates to an apparatus and method for delivering fluid with a controlled rate of flow. More particularly this invention relates to a simple, compact, inexpensive infuser which is capable of delivering a relatively constant dosage of an active agent at a controlled rate for parenteral delivery, and to a method for achieving such delivery of fluid.

2. Description of the Prior Art

Active agents are commonly administered to a subject parenterally either by injection or infusion. The commonly used distinction between the two is that an injection introduces a dosage of drug in a pulse form, either subcutaneously, intramuscularly, intravenously, or intraarterially, whereas an infusion introduces the active agent in a continuous manner over a prolonged period of time, such as, for example, in the conventional intravenous drip. It is generally more desirable to eliminate pulse dosages in which a relatively large amount of the active agent is rapidly deposited for consumption in the body over a prolonged period of time, in favor of the administration over long periods of time of smaller doses. Further it is highly desirable to infuse active agents to the patient at a constant, controlled rate.

The usual procedure for delivering fluids with a controlled rate of flow, for example, in the gradual parenteral administration of biological fluids, such as blood, plasma or medicinal solutions, such as drugs into the human body, was to use gravity-operated apparatus such as an intravenous infusion set. An intravenous infusion set comprises a bottle for the fluid which is supported in an inverted position at a higher level than the patient, an intravenous feed tube, typically of a plastic material and a resistor mechanism, such as a clamp operating on the plastic tube, the clamp being adjusted so as to allow the fluid to drip at a controlled rate into a drip chamber located below the bottle. The drip chamber allows a nurse or other attendant to observe the rate of flow of fluid from the bottle and to adjust the resistor to give a desired rate. It also creates a reservoir for the fluid at the lower end of the chamber to ensure that no air enters the main feeding tube leading to the patient. Because it is necessary to maintain the drip bottle at a substantially constant height above the patient, the conventional intravenous set is inconvenient for mobile use.

While an intravenous infusion set has several virtues, including simplicity, independence from external power supplies and adjustability over a wide range of flow rates, it is not entirely satisfactory because it is subject to variations in the flow rate produced. It is therefore necessary that the flow rate of the fluids delivered by the intravenous set be monitored frequently and adjusted as necessary to maintain the desired rate.

Various equipment has been designed to provide better control of flow rate, including, for example, devices which use servo controlled systems to drive a power unit for a pump, and to power in-line linear actuators which control the opening on the intravenous set. Such equipment is both complex and expensive.

More recently, self-driven pumps have been developed for the administration of active agents by infusion. One example of such a device is a pump driven by a constant force spring powered drive to provide a constant rate of fluid discharge, described in U.S. Pat. No. 4,202,333. This device is relatively expensive and the device is cumbersome to transport and is therefore cumbersome when used by ambulatory patients. Another such device incorporates a special constant rate elastomeric balloon in combination with a special intravenous set which includes a rate controlling orifice, described in U.S. Pat. Nos. 4,318,400 and 4,386,929. These devices are not entirely satisfactory because of the significant manufacturing tolerances involved to meet product functional requirements. For example, the physical properties and dimensions of the elastomeric balloon must be carefully controlled by provide the desired controlled flow rate. Changes in rubber durometer or tube wall thickness can materially affect fluid delivery rate. Further, the delivery rate may be adversely affected by variations in pressure on the elastomeric balloon resulting from changes in external pressure such as atmospheric pressure. Also, the elastomeric balloon may burst in actual use if not properly formulated, and this can be extremely hazardous, particularly in the case of chemotherapeutic drugs and the like. Additionally, the elastomeric balloon is not readily adapted to factory pre-filling and extended storage, particularly of medicinal fluids, because of chemical interaction between the elastomeric balloon and the fluid.

Another example of an apparatus for delivering fluids with a controlled rate of flow is described in U.S. Pat. No. 4,180,067. The apparatus includes an "actuator" which includes a vacuum power unit. The vacuum power unit includes a cylinder which is closed at one end and has a piston slidable therein. The piston in the cylinder of the vacuum power unit is coupled to a movable wall of a liquid storage container through a crosshead 15 which functions as a transmission mechanically coupling the separate piston of the liquid storage container to the piston in the cylinder of the vacuum power unit. The cylinder of the vacuum power unit is evacuated when the slidable piston is substantially at the open end of the cylinder so that atmospheric pressure acts upon the piston to drive it towards the closed end of the cylinder. That motion produces a reduction of the volume of the liquid storage container through the crosshead transmission which couples the piston in the vacuum cylinder to the movable wall of the container. This apparatus is rather cumbersome and complicated. The vacuum power unit and liquid storage unit are configured parallel to one another, and the apparatus relies on a two piston arrangement in combination with the transmission means connecting the two separate pistons to effect delivery of the liquid from the storage container. The apparatus does not provide a single plunger means to provide the power drive means and to effect discharge of the liquid from the apparatus.

Thus there remains a need for a simple, compact, inexpensive infuser which is capable of delivering fluid at a relatively constant and controlled rate of flow, which may be prefilled with medicinal liquids and stored, and which may be used by ambulatory patients.

Accordingly, it is a principal object of the present invention to provide an apparatus for delivering fluid at a relatively constant, controlled rate of flow. It is a related object to provide such an apparatus for delivering a medicinal liquid.

It is a further object of this invention to provide such an apparatus that is useful for introducing small amounts of a medicinal liquid to a patient over a prolonged period of time.

It is yet another object of this invention to provide such an apparatus that is compact and simple. A related object is to provide such a device that is portable and not cumbersome and is thus suitable for use by ambulatory patients.

It is a further object of the present invention to provide an apparatus for delivering fluid at a relatively constant, controlled rate of flow which can be prefilled with medicinal fluids and stored for an extended period of time, ready for use.

These and other objects of the invention will be readily apparent from the following description with reference to the accompanying drawings.

SUMMARY OF THE INVENTION

The present invention provides a vacuum powered apparatus for delivering fluid with a relatively constant, controlled rate of flow. As used herein, the term vacuum power or vacuum powered means the driving force on a movable wall caused by a differential in pressure between atmospheric pressure on one side of the movable wall and a second pressure, which is less than atmospheric pressure, on the other side of the movable wall.

The apparatus of the present invention includes a vacuum power means for driving a fluid to be delivered from the apparatus, a fluid storage means carried in axial alignment with the vacuum power means and adapted to carry fluid to be delivered by the apparatus, and a plunger means carried by the vacuum power means in axial communication with the fluid storage means. The vacuum power means is open to the atmosphere at one end, and at the other end is sealed from the atmosphere. The vacuum power means includes a sealed portion which comprises at least a partial vacuum. The plunger means forms a movable wall which sealingly and slidingly engages the sealed portion of the vacuum power means and is disposed in the vacuum power means so that the movable wall forms an end wall of the sealed portion of the vacuum power means. The sealed portion of the vacuum power means is at least partially evacuated when the plunger means is substantially at the open end of the vacuum power means, and atmospheric pressure acts upon the plunger means to drive it towards the sealed end of the vacuum means. When the orifice in the fluid storage means is opened, atmospheric pressure acting on the plunger means drives the movable wall of the plunger means toward the sealed end of the vacuum power means and directly drives the plunger means toward the orifice of the fluid storage means to thereby drive the fluid contained in the fluid storage means through the orifice to deliver the fluid from the apparatus.

DESCRIPTION OF THE DRAWINGS

FIGS. 5 and 6 are sectional views of a valve arrangement and an unlocking mechanism for the orifice of the fluid storage means. FIG. 5 shows the valve in the closed position and the unlocking mechanism partially inserted and in sealing engagement with the valve. FIG. 6 shows the unlocking mechanism fully inserted into the valve and the valve in the open position.

DETAILED DESCRIPTION OF THE PREFERRED EMBODIMENTS

Figure 1:
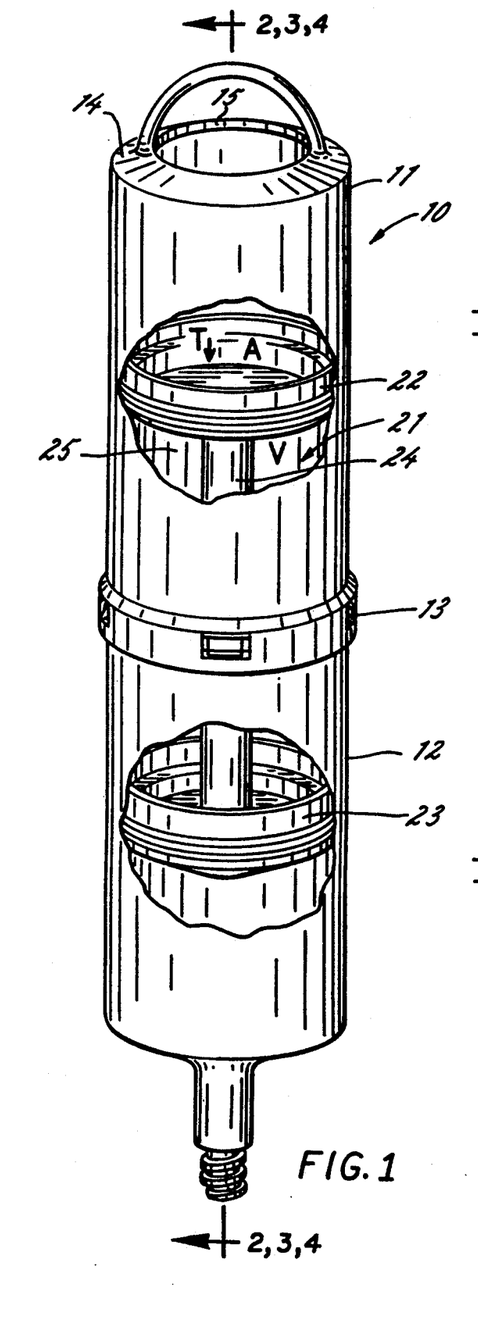
FIG. 1 is a perspective view of the vacuum powered fluid delivery apparatus of the present invention with a partial cut-away view of the interior of the vacuum power means and the fluid storage means showing the axial alignment thereof and the plunger means axially aligned in both the vacuum power means and the fluid storage means.

In accordance with the invention there is provided a vacuum powered apparatus 10 for the delivery of fluid with a relatively constant, controlled rate of flow, wherein the vacuum power means for driving fluid from the apparatus and the fluid storage means are axially aligned as is illustrated in FIG. 1. The vacuum powered apparatus 10 includes a vacuum power drive means (or chamber) 11 and a separate fluid storage means 12 which may be mounted to the vacuum power drive means 11 by any suitable means sufficient to hold the vacuum power drive means 11 and the fluid storage means 12 together during operation of the device. In the embodiment illustrated in FIGS. 1–4, the vacuum power drive means and fluid storage means are detachably secured together by a bayonet mount, generally shown at 13. It will be appreciated that the vacuum power means and the fluid storage means may be permanently secured, as for example by spot welding or the like at the bayonet joint.

Vacuum power drive means 11 has a first end 14 which forms an opening 15 to expose the interior of vacuum power means 11 to atmospheric pressure, and a second end 16 which is sealed from the atmosphere. The sealed end 16 forms an opening 17 for sealingly receiving a plunger means.

The fluid storage means 12 is adapted to carry the fluid to be delivered by the apparatus, and is disposed in axial alignment with the vacuum power means 11. In the illustrative and preferred embodiment, the fluid storage means 12 is separate from the vacuum power means 11 and is detachably connected to the vacuum power means in axial alignment with the vacuum power means. The separate and detachable nature of the fluid storage means provides the apparatus with substantial flexibility in that the same vacuum power drive means can be used repeatedly, with different fluid storage means to deliver different fluids and for different delivery conditions. The fluid storage means has two ends 18, 19. End 18 forms an orifice 20 for controlling delivery of fluid from the apparatus. The second end 19 is adapted to receive a plunger means as will be described more fully hereinafter.

The vacuum power means 11 has a plunger means 21 disposed therein in sealing and sliding engagement with the walls of the vacuum power means. The plunger means 21 is in axial communication with both the vacuum power means 11 and the fluid storage means 12. During operation of the device, the plunger means both receives the thrust of atmospheric pressure which acts on the plunger means at the open end 14 of the vacuum power means 11, and, in turn provides the driving means to drive fluid from the fluid storage means.

In the illustrative embodiment, FIGS. 1–4, plunger means 21 includes a first head 22 which forms a movable wall in the vacuum power means 11. The first head 22 sealingly and slidingly engages the side walls of the vacuum power means to allow at least a partial vacuum to be drawn in the portion of the vacuum power means 11 swept by the first head 22 as it is moved from the sealed end 16 toward the open end 14 of vacuum power means 11. Plunger means 21 further includes a second head 23 and a rod means 24 for connecting first head 22 and second head 23. The rod means 24 extends through the opening 17 in the sealed end 16 of vacuum power means 11 so that the second head 23 of plunger means 21 may communicate with the open end 19 of fluid storage means 12. The second head 23 of plunger means 21 is preferably configured to fit sealingly and slidably into the open end 19 of fluid storage means 12.

Figure 3:
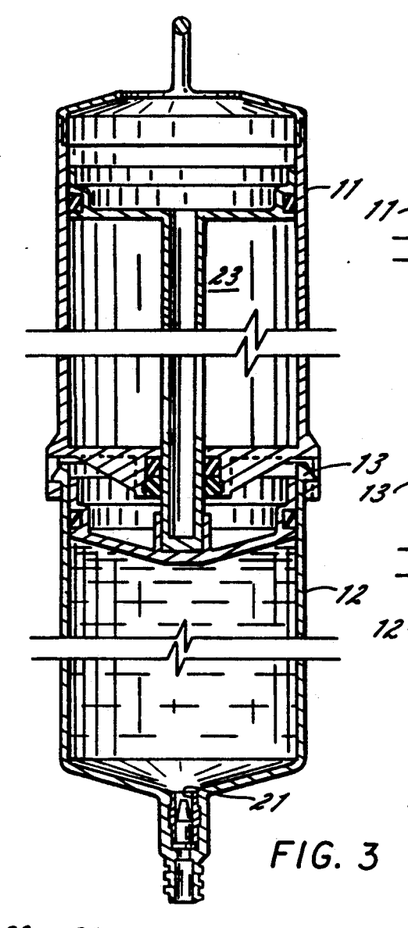
FIG. 3 is a sectional view of the apparatus taken along line 3—3 of FIG. 1 and showing the vacuum power means and the fluid storage means detachably secured to one another with the plunger means located at the open end of the vacuum power means and in the activated position ready to deliver fluid.
Figure 4:
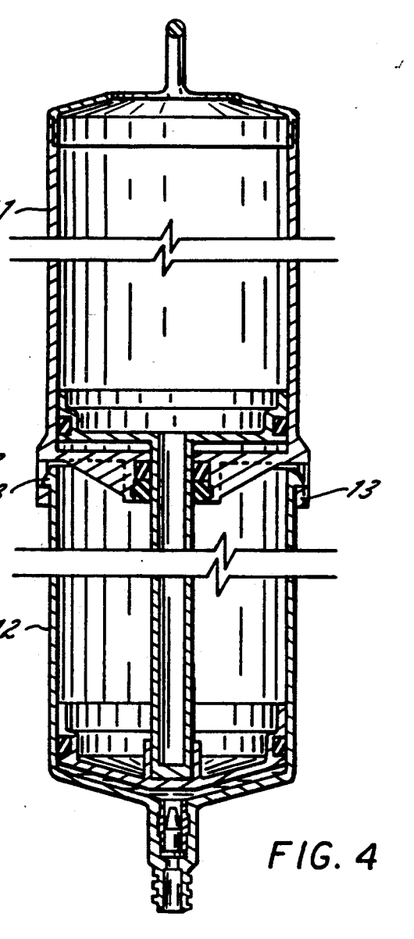
FIG. 4 is a sectional view of the apparatus taken along line 4—4 of FIG. 1 and showing the vacuum power means and the fluid storage means detachably secured to one another with the plunger means located at the sealed end of the vacuum power means and in the inactive position.

As first head 22 of plunger means 21 is moved from a position at or near sealed end 16 of vacuum power means 11, as shown in FIG. 4, to a position substantially at the open end 14 near the opening 15 in vacuum power means 11, as shown in FIG. 3, a portion 25 of the vacuum power means 11 between the first head 22 and sealed end 16 of the vacuum power means 11 is swept by first head 22. The portion 25 swept by first head 22 is thus at least partially evacuated, i.e., at least a partial vacuum is formed in the sealed evacuated portion 25 of vacuum power means 11. When first head 22 of plunger means 21 has been moved so as to form sealed evacuated portion 25, the apparatus is activated, that is, it is capable of delivering fluid. It is preferred that first head 22 of plunger means 21 seat as closely as possible to the sealed end 16 of vacuum power means 11 in order to minimize the volume of air contained in the vacuum power means 11 between first head 22 and the sealed end 16 and thereby minimize the volume of air in sealed evacuated portion 25 of the vacuum power means after first head 22 has swept through the vacuum power means. Under such conditions, after the first head 22 has been moved to the activated position, the vacuum in the sealed evacuated portion 25 of vacuum power means is maximized. It will be appreciated that the degree of vacuum in sealed evacuated portion 25 is not critical to the operation of the apparatus so long as atmospheric pressure can act on first head 22 of plunger means 21 to cause the vacuum in sealed evacuated portion 25 to collapse as a result of the energy differential between atmospheric pressure on one side (A in FIG. 1) of first head 22 and the vacuum on the other side (V in FIG. 1) of first head 22 to allow the plunger means 21 to drive fluid from the apparatus at a relatively constant rate simultaneously with the collapse of the vacuum for the entire volume of fluid to be delivered from the apparatus. In the preferred embodiment of the present invention the internal gases in the sealed portion of the chamber are minimized so as to maximize the vacuum, and to thereby provide the greatest and most constant energy differential.

When the orifice 20 of fluid storage means 12 is opened, atmospheric pressure acting upon first head 22 of plunger means 21 with thrust T will cause the vacuum in the sealed evacuated portion 25 of the vacuum power means 11 to collapse. As that vacuum collapses, first head 22 of plunger means 21 is driven toward the sealed end 16 of vacuum power means 11. As first head 22 is driven toward sealed end 16 of vacuum power means 11, rod means 24 of plunger means 21 slides through opening 17 in sealed end 16 of vacuum power means 11 to drive second head 23 toward the orifice end 18 of the fluid storage means 12 to thereby drive fluid out of the orifice 20 for delivery. As illustrated in FIG. 4, and in the preferred embodiment of the present invention, when the first head 22 of plunger means 21 comes to rest at or near the sealed end 16 of vacuum power means 11, the second head 23 of plunger means 21 is at rest at the orifice end 18 of fluid storage means 12 so that the fluid to be delivered is discharged from fluid storage chamber 12.

In an alternative embodiment of the present invention, fluid storage means 12 includes at its open end 19 a movable end wall (not shown) in sealing and sliding engagement with the side walls of fluid storage means 12. The rod means 24 of plunger means 21 may then terminate in a blunt end (not shown) that engages the movable end wall of fluid storage means 12. As atmospheric pressure acts upon the first head 22 of plunger means 21 to cause the vacuum in sealed evacuated portion 25 to collapse, first head 22 is driven toward the sealed end 16 of vacuum power means 11, and the blunt end of rod means 24 engages the movable end wall of the fluid storage means 12 to drive the movable end wall of the fluid storage means 12 toward the orifice end 18 of fluid storage means 12 to thereby deliver liquid from the apparatus.

Figures 11, 12:
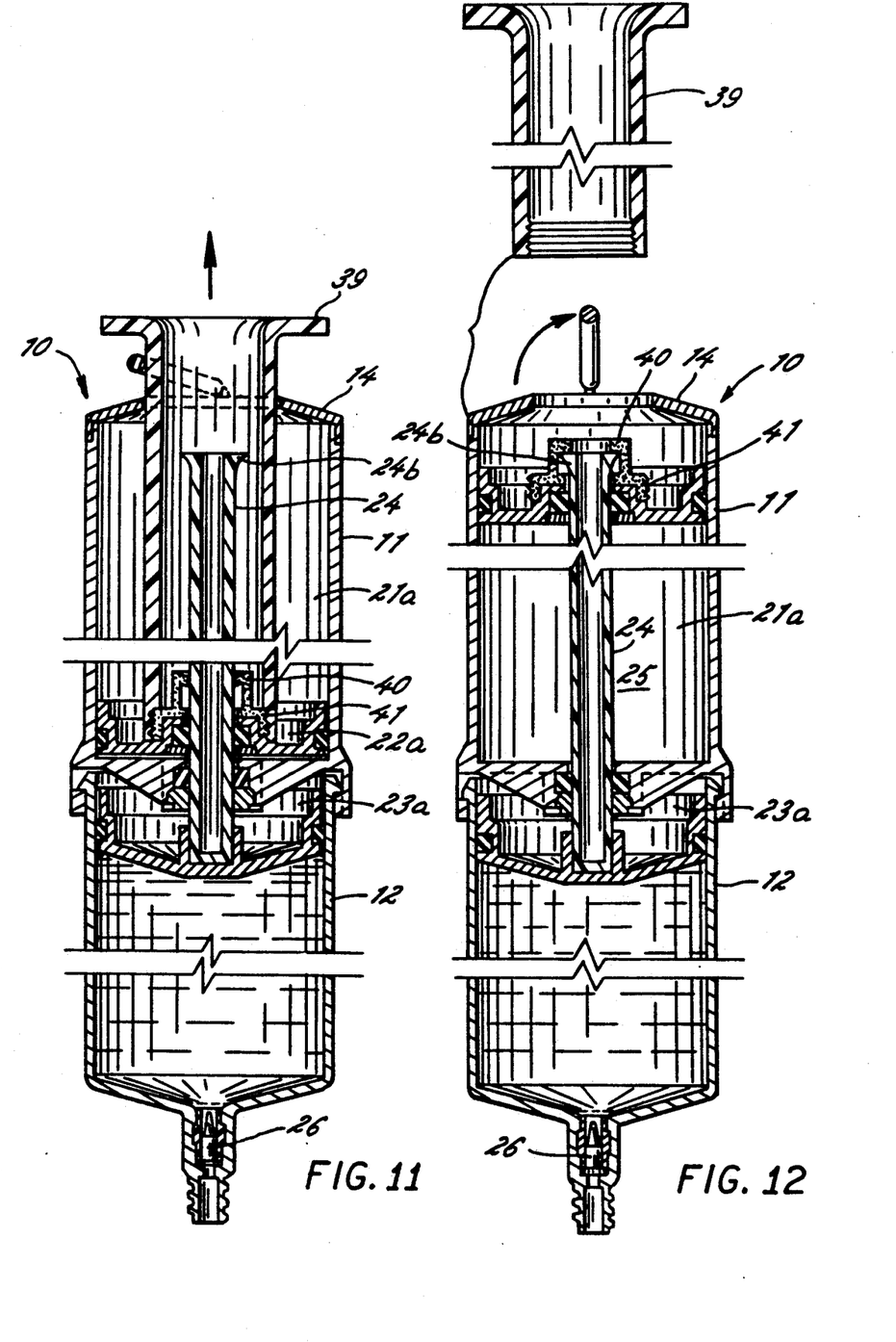
FIG. 11 is a side view of another alternative embodiment of the vacuum powered fluid delivery apparatus of the present invention showing a prefilled fluid storage means and the vacuum power means in the inactive position.
FIG. 12 is a side view of the embodiment shown in FIG. 11 with the vacuum power means in the activated position and the apparatus ready for the delivery of fluid.

An alternative embodiment of the apparatus described above is shown in FIGS. 11 and 12. This embodiment operates in substantially the same way as the embodiment illustrated in FIGS. 1–4. However, the apparatus in accordance with this embodiment as illustrated in FIGS. 11 and 12 may be assembled with fluid storage means prefilled with the desired medicinal liquid, and with an inactive vacuum power drive, which may be activated immediately prior to use. The primary difference between the embodiment of FIGS. 1-4 and the embodiment of FIGS. 11 and 12 lies in the configuration of the plunger means, in the provision of a handle means to activate the apparatus, and in the fact that the fluid storage means may be prefilled.

In accordance with the embodiment of the invention illustrated in FIGS. 11 and 12, plunger means 21a includes a first head 22a, a second head 23a and rod means 24a for connecting the first head 22a and second head 23a. The first head 22a is in sealing and sliding assembly with rod means 24a so that it may move up and down along rod means 24a. The first head 22a includes means for engaging the rod means when the first head 22a is substantially at the open end 14 of the vacuum power means 11 (FIG. 12). Handle means 39 are secured to first head 22a to permit first head 22a to be moved toward the open end 14 of the vacuum power means 11 to place plunger means 21a in the activated position (FIG. 12). As illustrated in FIGS. 11 and 12, the engaging means carried by the first head 22a are resilient fingers 40 which are capable of engaging and gripping a flanged portion 24b of rod means 24a. The engaging means 40 further include threads 41 for threadingly mating with the handle means 39. Thus, as illustrated in FIG. 11, handle means 39 is threaded to the first head 22a via threads 41. As in the embodiment illustrated in FIG. 1-4, first head 22a also sealingly and slidingly engages the side walls of vacuum power means 11 and forms a movable wall in vacuum power means 11 to allow at least a partial vacuum to be drawn in the portion of the vacuum power means 11 swept by first piston head 22a as it is moved up along rod means 24a from a point at or near sealed end 16 to a point at or near the open end 14 of vacuum power means 11.

FIG. 11 shows the apparatus in a prefilled, inactive condition, while FIG. 12 shows the apparatus in an active condition ready to deliver fluid. In order to activate the inactive apparatus shown in FIG. 11, handle means 39 is moved in the direction of the open end 14 of vacuum power means 11. As handle means 39 is so moved, first head 22a moves from its position at or near the sealed end 16 toward the open end 14 of vacuum power means 11. Handle means 39, and thus first head 22a must be moved in the direction of the open end 14 of vacuum power means 11 sufficiently so that engaging means 40 grip the rod means 24a. After the apparatus is activated, atmospheric pressure acting on the side of first head 22a exposed to the opening 15 will drive first head 22a toward sealed end 16. When the orifice 20 in fluid storage means 12 is opened, the force of the atmospheric pressure acting on first head 22a will collapse the vacuum in sealed portion 25 and the plunger means 21a will be driven toward the orifice force fluid from the orifice. It will be appreciated that fluid storage means 12 may form a housing for a container for holding the fluid to be delivered from the apparatus. The fluid container, which is carried in the housing, may have collapsible walls which will collapse under the force of the plunger means acting on the container to deliver fluid from the apparatus.

One advantage of the embodiment of the invention illustrated in FIGS. 11 and 12 is that the apparatus may be prefilled, for example, by the manufacturer, or pharmacist, with medicinal fluid and stored for the shelf life of that fluid. The apparatus stands ready for activation and immediate use, thereby eliminating the need for either a nurse or the patient to handle the medicinal fluid to be administered.

Figure 5:
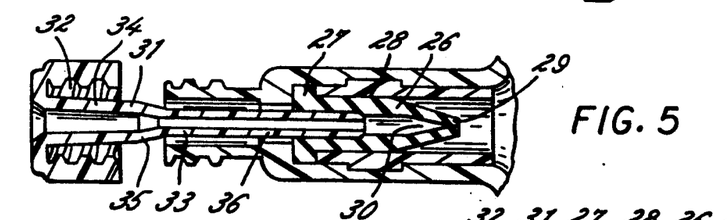
Figure 6:
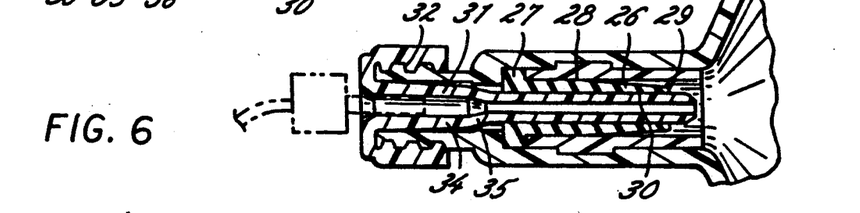

In keeping with a preferred embodiment of the present invention, the orifice 20 of fluid storage means 12 of either the embodiment illustrated in FIGS. 1-4 or in FIGS. 11 and 12 includes an elastomeric duck bill valve 26 as shown in greater detail in FIGS. 5 and 6. The valve 26 is normally closed, as shown in FIG. 5 to prevent fluid from leaking out of fluid storage means 12. The duck bill valve 26 generally comprises an end flange portion 27, an elongated central portion 28 which terminates in a tapered end portion 29, and a lumen 30 which extends from the flange portion 27 to the tapered end portion 29. The tapered end portion 29 provides a seal by which the valve 26 is normally closed.

Figure 2:
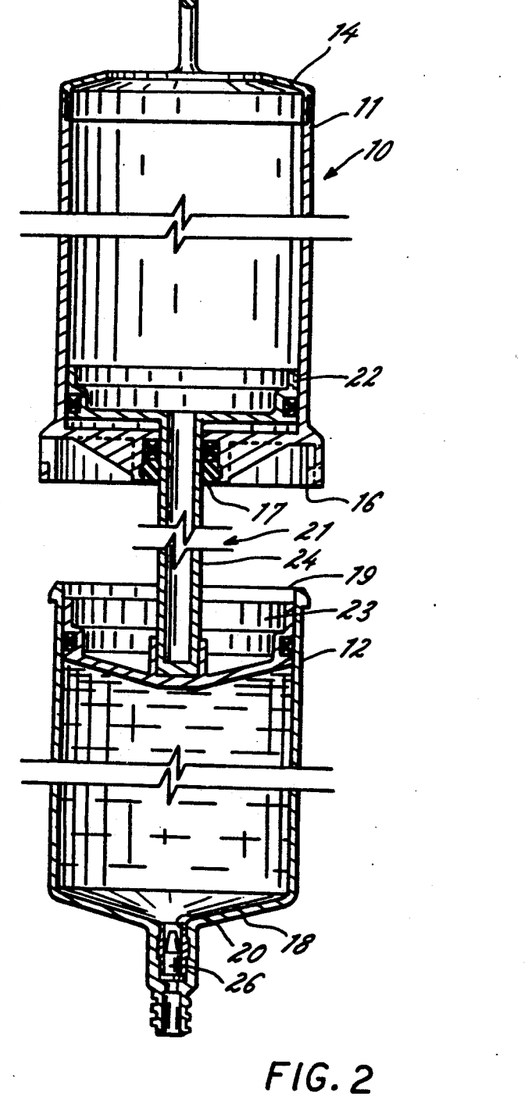
FIG. 2 is a sectional view of the apparatus taken along line 2—2 of FIG. 1 and showing the vacuum power means and the fluid storage means detached from one another and ready for assembly.

The vacuum powered apparatus of the present invention as illustrated in FIGS. 1-4 may be assembled either in an inactive, unfilled form and then filled to activate it, or in an activated filled form or as described above in connection with the embodiment illustrated in FIGS. 11 and 12, it may be assembled in a prefilled, inactive condition. As shown in FIG. 2, the apparatus of the present invention may be assembled in an activated, filled condition by first filling the fluid storage means 12 with the desired fluid, causing the open end 19 of the fluid storage means to engage the second head 23 of plunger means 21 and forcing the vacuum power means 11 and fluid storage means 12 together until they mate and are secured together with the bayonet mount 13. As the vacuum power means 11 and the fluid storage means 12 are forced together, the fluid in fluid storage means 12 acts against the second head 23 of plunger means 21 to bias the second head 23 toward vacuum power means 11 and thereby to drive the first head 22 toward the open end 14 of vacuum power means 11. As the first head 22 of plunger means 21 moves toward open end 14 of vacuum power means 11, the portion 25 of the vacuum power means 11 swept by the first head 22 is at least partially evacuated, that is, at least a partial vacuum is formed therein.

As shown in FIG. 4, the apparatus of the present invention may be assembled in an inactive, unfilled condition by attaching fluid storage means 12 to vacuum power means 11 and subsequently filling the fluid storage means with the fluid to be delivered. Filling fluid storage means 12 drives the second head 22 of plunger means 21 toward vacuum power means 11 and drives the first head 22 toward open end 14 of vacuum power means 11. The portion 25 of the power chamber 11 swept by the first head 22 will be at least partially evacuated and thus forms at least a partial vacuum therein.

In a preferred embodiment of the present invention, when the valve arrangement is the elastomeric duck bill valve 26 shown in FIGS. 3-6, fluid storage means 12 is filled using a male lure opening of a conventional intravenous syringe and a fluid filled syringe. The male lure is attached to a female lure opening of the fluid storage means 12 in locking and sealing engagement. As the male lure is pushed into the duck bill valve 26, the tapered end portion 29 opens to allow fluid to pass through the valve and into the fluid storage means. As the fluid contained in the syringe is injected into fluid storage means 12, the force of the injected fluid forces the second head 23 on plunger means 21 toward vacuum power means 11 and at the same time forces the first head 22 of plunger means 21 to move toward the open end 14 of vacuum power means 11. As the first head 22 moves toward open end 14 of vacuum power means 11, the first head 22 sweeps a portion of the vacuum power means 11 to create sealed evacuated portion 25 to thereby create at least a partial vacuum therein. After the fluid has been discharged from the injection syringe, the male lure and syringe are removed and the valve 26 closes. The apparatus is thus activated and in condition for delivering fluid as shown in FIG. 3.

In another alternative embodiment (not shown) the fluid storage means may be equipped with a separate fill port through which the fluid to be delivered by the apparatus is injected to fill the fluid storage means and activate the apparatus in the same manner as described above.

In keeping with another preferred embodiment of the present invention, a combination male lure 31 and fluid administration set is provided for opening the duck bill valve 26 and further controlling the rate at which fluid is delivered by the apparatus. The male lure 31 includes a threaded end portion 32 for threadingly engaging a threaded end portion of the fluid storage means 12. Male lure 31 includes an elongated tube 33 having a portion 34 of one diameter which tapers at 35 to an elongated portion 36 having a smaller diameter than the first diameter portion 34. The elongated portion 36 of male lure 31 has a diameter such that the elongated portion can press fit into the lumen 30 of duck bill valve 26 to form a seal between the smaller diameter portion 36 of male lure 31 and the elastomeric material of the duck bill valve 26. When the smaller diameter portion 36 of male lure 31 is advanced into valve 26 sufficiently, the tapered portion 29 of duck bill valve 26 is opened, thereby permitting fluid to exit from the fluid storage means 12 and into the lumen 30 of male lure 31. At the threaded end 32 of the male lure 31 there is provided a fluid administration set of conventional and well known design. Such administration sets are available with flow restrictive orifices of a fixed or adjustable design to further control the flow rate of the fluid delivered from the fluid delivery apparatus herein described.

In an alternative embodiment of the invention as illustrated in FIGS. 7-10, the vacuum powered apparatus 90 includes a vacuum power drive means 100, a separate fluid storage means 112 for storing the fluid to be delivered by the apparatus and a receptacle 102 carried by the vacuum power drive means 100 for receiving fluid storage means 112 so that the vacuum power means 100 and fluid storage means 112 are in axial alignment. In the preferred embodiment shown in FIGS. 7-10, receptacle 102 is formed as an integral extension of vacuum power means 100. Receptacle 102 includes a cylindrical wall 103 extending from vacuum power means 100 and an end wall 104. Cylindrical wall 103 and end wall 104 define a cavity 105 for receiving fluid storage means 112. End wall 104 of receptacle 102 includes an opening 106 for receiving the orifice end of fluid storage means 112. Fluid storage means 112 is placed in cavity 105 of receptacle 102 to ready the apparatus for fluid delivery.

It will be appreciated that fluid storage means 112 is not limited to the illustrated embodiment. On the contrary, fluid storage means 112 may have a variety of shapes and may be made of a variety of materials while still providing a vacuum powered apparatus for delivering fluid with a relatively constant controlled rate of flow. Thus, while in the illustrative embodiment fluid storage means 112 is a cylindrical, rigid chamber, the fluid storage means may comprise a flexible container that has collapsible walls which will collapse under the force of plunger means acting on the container.

Vacuum power means 100 has a first end 114 which forms an opening 115 to expose the interior of vacuum power means 100 to atmospheric pressure, and a second end 116 which is sealed from the atmosphere. The sealed end 116 forms an opening 117 for sealingly receiving a plunger means.

The fluid storage means 112 is adapted to carry the fluid to be delivered by the apparatus and is in axial alignment with vacuum power means 100 when placed in the cavity 105 of receptacle 102. In the illustrative and preferred embodiment, fluid storage means 112 is separate from vacuum power means 100. The separate nature of the fluid storage means provides the apparatus with substantial flexibility in that the same vacuum power means can be used repeatedly, with different fluid storage means to deliver different fluids and for different delivery conditions.

Fluid storage means 112 has two ends 118, 119 End 118 forms an orifice 120 for controlling the delivery of fluid from the apparatus. The second end 119 is adapted to receive a plunger means as will be described more fully hereinafter. The fluid storage means 112 preferably includes a movable wall 130 at the second end thereof in sealing and sliding engagement with the walls of the fluid storage means. Movable wall 130 provides, in effect, a cover for fluid storage means 112.

Figures 7, 8:
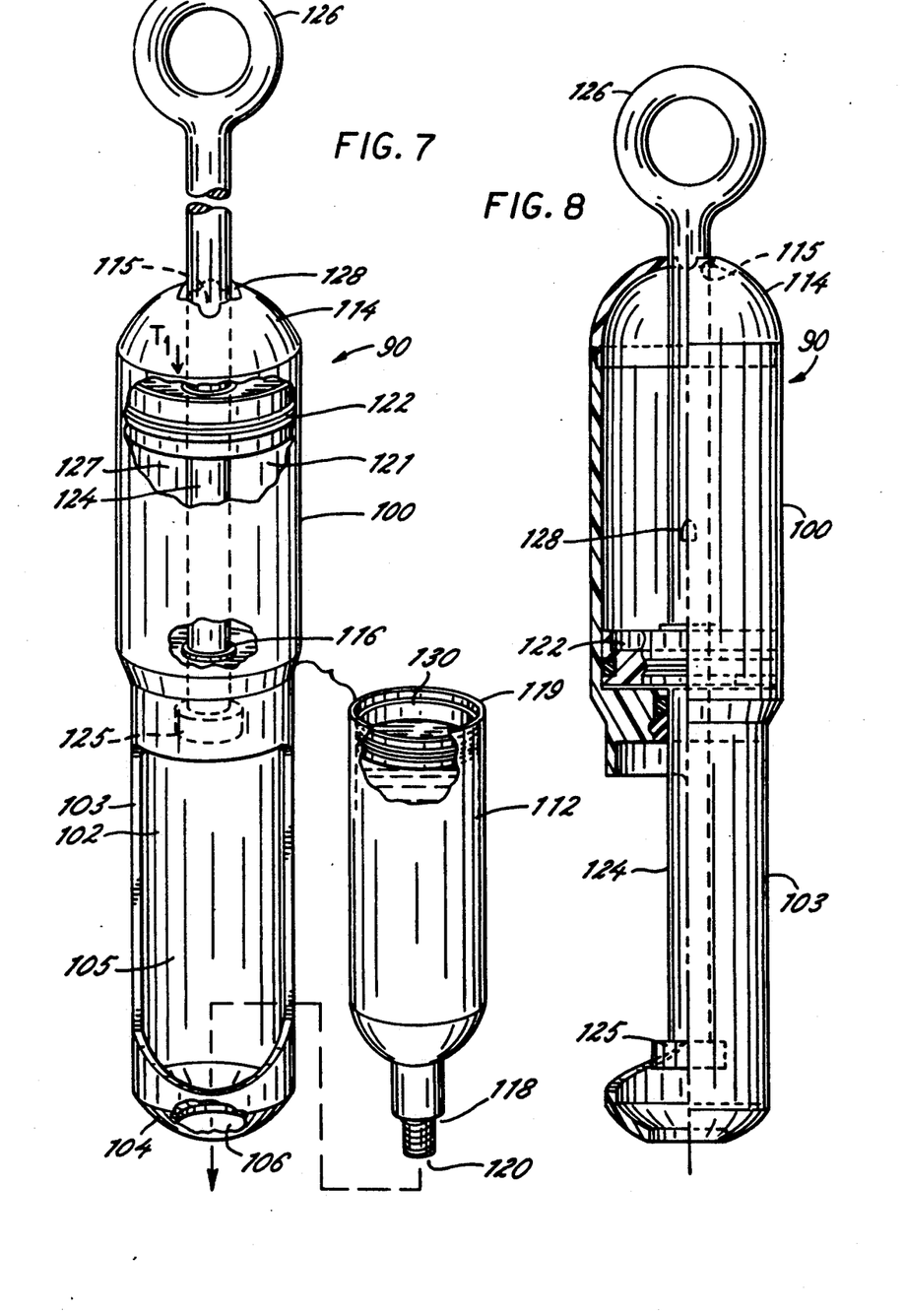
FIG. 7 is a perspective view of an alternative embodiment of the vacuum powered fluid delivery apparatus of the present invention with a partial cut-away view of the interior of the vacuum power means showing the plunger in the activated position, and a fluid storage means containing the fluid to be delivered separately and ready for insertion into a receptacle of the apparatus.
FIG. 8 is a side view of the apparatus shown in FIG. 7, in section, with the plunger means in the inactive position.
Figure 9:
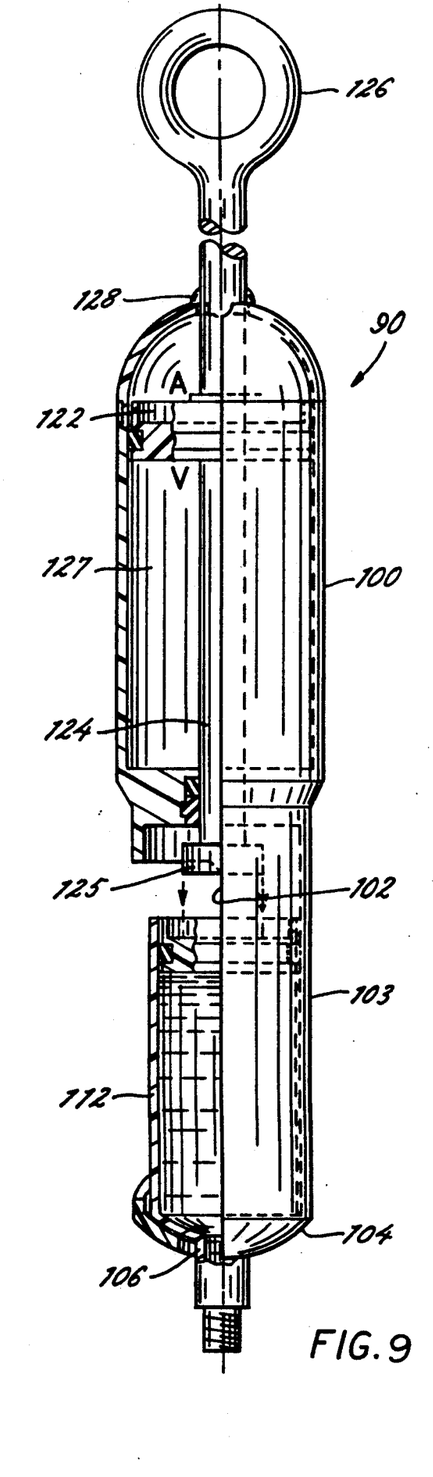
FIG. 9 is a side view of the apparatus shown in FIG. 7, in section, with the plunger means in the activated position and the fluid storage means in position for delivery of fluid.

The vacuum power means 100 has a plunger means 121 disposed therein in sealing and sliding engagement with the walls of vacuum power means 100. Plunger means 121 is in axial communication with both vacuum power means 100 and fluid storage means 112. In the illustrative embodiment, plunger means 121 includes a first head 122 which sealingly and slidingly engages the side walls of the vacuum power means 100 to allow at least a partial vacuum to be drawn in the portion of the vacuum power means 100 swept by the first head 122 as it is moved from a position at or near the sealed end 116 of the vacuum chamber 100 toward the open end 114 of vacuum power means 100. Plunger means 121 further includes rod means 124 which extends out of sealed end 116 of the vacuum power means 100 through sealed opening 117 of vacuum power means 100. Rod means 124 of plunger means 121 is capable of communicating with fluid storage means 112. As shown, rod means 124 terminates in a blunt end 125 which engages the movable wall 130 of fluid storage means 112. Rod means 124 further includes handle means 126 to permit plunger means 121 to be drawn in a direction toward the open end 114 of vacuum power means 100 to evacuate a portion 127 of the vacuum means and thereby create at least a partial vacuum in portion 127. In the preferred embodiment, handle means 126 includes locking means 128 to lock handle means 126 in the activated position. In the illustrated embodiment, locking means 128 forms a tab which engages the outer surface 131 of the vacuum power means 100 when handle means 126 is twisted as shown in FIG. 7. During operation of the device, plunger means 121 both receives the thrust of atmospheric pressure which acts on the first head 122 of plunger means 121 at the open end 114 of the vacuum power means 100, and, in turn provides the driving means to drive fluid from the fluid storage means.

As the first head 122 of plunger means 121 is moved from a position at or near sealed end 116 of vacuum power means 100, as shown in FIG. 8, to a position substantially at or near the open end 114, near the opening 115 in vacuum power means 100, as shown in FIG. 7, a portion 127 of the vacuum power means 100 between the first head 122 of plunger means 121 and sealed end 116 of vacuum power means 100 is swept by first head 122. The portion 127 of vacuum power means 100 is thus at least partially evacuated, i.e., at least a partial vacuum is formed in sealed evacuated portion 127 of vacuum power means 100. When the first head 122 of plunger means 121 has been moved so as to form sealed evacuated portion 127, the apparatus is activated, i.e., it is capable of delivering fluid. As in the embodiment illustrated in FIGS. 1-4, it will be appreciated that the degree of vacuum in sealed evacuated portion 127 of vacuum power means 100 is not critical to the operation of the apparatus so long as atmospheric pressure can act on the first head 122 of plunger means 121 to cause the vacuum in sealed evacuated portion 127 to collapse as a result of the energy differential between atmospheric pressure on one side (A in FIG. 9) of first head 122 and the vacuum on the other side (V in FIG. 9) of first head 122 to allow plunger means 121 to drive fluid from the apparatus at a relatively constant rate simultaneously with the collapse of the vacuum, for the entire volume of fluid to be delivered from the apparatus.

In the preferred embodiment of the present invention, the internal gases in the sealed portion of the chamber are minimized so as to maximize the vacuum, and to thereby provide the greatest and most constant energy differential. It is thus preferred that first head 122 of plunger means 121 seat as closely as possible to the sealed end 116 of vacuum power means 100 in order to minimize the volume of air contained in vacuum power means 100 between first head 122 and sealed end 116 of vacuum power means 100 and thereby minimize the volume of air in sealed evacuated portion 127. Under such conditions, after the first head 122 of plunger means 121 has been moved to the activated position, the vacuum in the sealed evacuated portion 127 of vacuum power means 100 is maximized.

Figure 10:
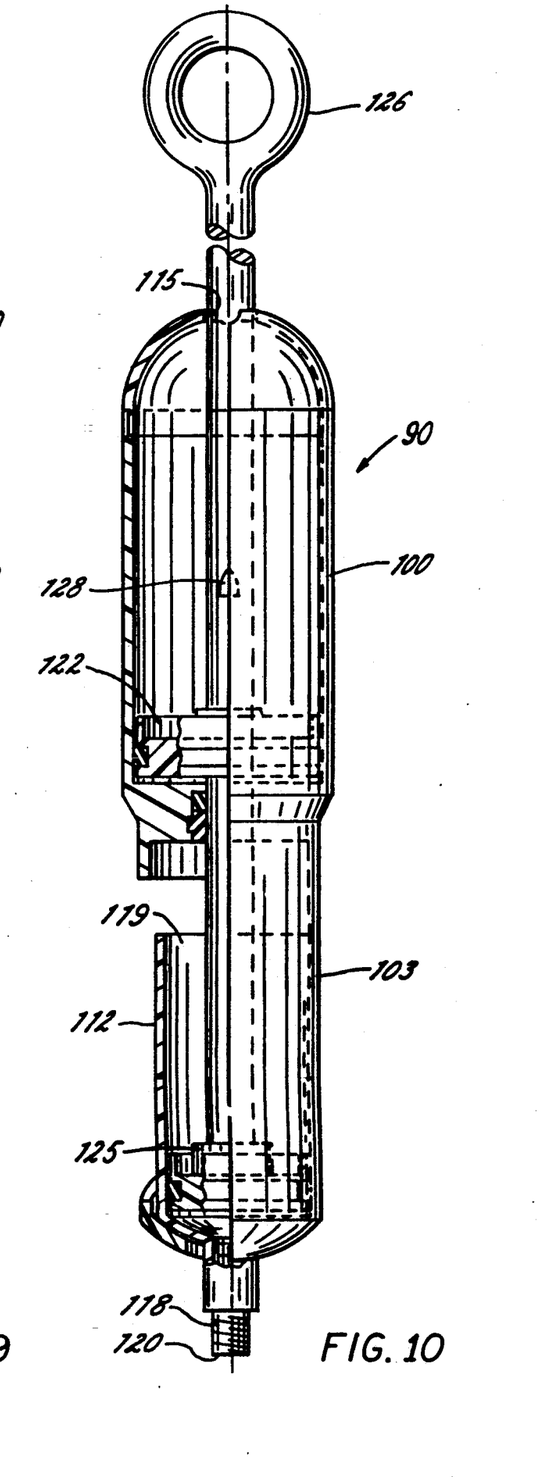
FIG. 10 is a side view of the apparatus of FIG. 7, in section, illustrating the position of the plunger means in the respective vacuum power means and fluid storage means after fluid delivery.

When the orifice 120 of fluid storage means 112 is opened, handle means 126 is twisted to unlock locking means 128 and atmospheric pressure acting upon first head 122 of plunger means 121 with thrust $T_1$ causes the vacuum in sealed evacuated portion 127 to collapse. As that vacuum collapses, first head 122 is driven toward sealed end 116 of vacuum power means 100. As first head 122 is driven toward sealed end 116, rod means 124 of plunger means 121 slides through opening 117 in sealed end 116 to drive blunt end 125 of plunger means 121 toward fluid storage means 112 to engage the movable wall 130 of fluid storage means 112. Since vacuum power means 100 and fluid storage means 112 are in axial alignment, and plunger means 121 is in axial communication with both the vacuum power means and the fluid storage means, both plunger means 121 and movable wall 130 are simultaneously and directly driven toward orifice end 118 of fluid storage chamber 112 to thereby drive fluid out of orifice 120 for delivery. As illustrated in FIG. 10, when first head 122 of plunger means 121 comes to rest at or near sealed end 116 of vacuum power means 100, movable wall 130 is at rest at or near orifice end 118 of fluid storage means 112, and the fluid to be delivered is discharged from the fluid storage means.

The orifice 120 of fluid storage means 112 may include an elastomeric duck bill valve as described previously with respect to the embodiment illustrated in FIGS. 1-6. Further a combination lure lock and administration set may be used in combination with this alternative embodiment to further control the rate at which fluid is delivered from the apparatus.

The present invention thus provides a compact inexpensive apparatus for delivering fluid with a relatively constant, controlled rate of flow, and which is particularly adapted for use by ambulatory patients.

I claim as my invention:

1. An apparatus for delivering fluid with a relatively constant, controlled rate of flow comprising, in combination a first chamber comprising a vacuum power chamber for driving the fluid to be delivered from the apparatus, said first chamber comprising a sealed portion comprising at least a partial vacuum, a separate second chamber comprising a fluid storage chamber adapted to receive a fluid, said second chamber being mounted to said first chamber in axial alignment with said first chamber, said plunger means carried in said first chamber to effect delivery of fluid from the apparatus, said plunger means comprising a rod means and first head, said first head forming a movable wall of said sealed portion in sealing and sliding engagement with said first chamber, said first chamber having a first end open to the atmosphere, and a second end sealed to the atmosphere, said plunger means being disposed in said first chamber so that the movable wall of said plunger means forms one end of the sealed portion, and said rod means being connected to said first head and extending from the sealed end of said first chamber in axial communication with said second chamber, said first head being in sealing and sliding assembly with said rod means and including engaging means for engaging said rod means when said first head is substantially near the open end of said first chamber, handle means secured to said first head to permit said first head to be moved forward said open end of said first chamber to allow said engaging means to engage said rod means, said second chamber having a first end for receiving the rod which extends from said first chamber and a second end forming an orifice through which fluid is delivered, the first chamber being evacuated when the movable wall of said plunger means is substantially at the open end of the first chamber so that atmospheric pressure acts upon said plunger means to drive it toward the sealed end of said first chamber, whereby when the orifice in said second chamber is opened, atmospheric pressure acting upon said plunger means drives the movable wall of the plunger toward the sealed end of the first chamber and drives the rod received by the second chamber toward the orifice of the second chamber through the orifice to deliver the fluid from the apparatus.

2. The apparatus of claim 1 wherein said second chamber comprises a housing for receiving a flexible container capable of carrying fluid to be delivered by said apparatus, said flexible container having collapsible walls and being carried in said housing.

3. The apparatus of claim 2 wherein said apparatus includes a fluid administration set in communication with said orifice for further controlling the rate of flow of fluid from said apparatus.

4. The apparatus of claim 1 wherein said orifice in said second chamber includes valve means.

5. The apparatus of claim 4 wherein said apparatus includes a fluid administration set in communication with said orifice for further controlling the rate of flow of fluid from said apparatus.

6. An apparatus for delivering fluid with a relatively constant, controlled rate of flow comprising, in combination, a first chamber comprising a vacuum power chamber for driving the fluid to be delivered from the apparatus, said first chamber comprising a sealed portion comprising at least a partial vacuum, a separate second chamber comprising a fluid storage chamber adapted to receive a fluid, said second chamber being mounted to said first chamber in axial alignment with said first chamber, and plunger means carried in said first chamber to effect delivery of fluid from the apparatus, said plunger means forming a first chamber movable wall of said sealed portion in sealing and sliding engagement with said first chamber, said first chamber having a first end open to the atmosphere, and a second end sealed to the atmosphere, said plunger means being disposed in said first chamber so that the first chamber movable wall of said plunger means forms one end of the sealed portion, and said plunger means having a portion thereof extending from the sealed end of said first chamber in axial communication with said second chamber, said second chamber having a first end for receiving the portion of said plunger means which extends from said first chamber and a second end forming an orifice through which fluid is delivered, said second chamber including at its first end a second chamber movable end wall in sealing and sliding engagement with said second chamber, said second chamber movable end wall being capable of receiving said plunger means, the first chamber being evacuated when the first chamber movable wall of said plunger means is substantially at the open end of the first chamber so that atmospheric pressure acts upon said plunger means to drive it toward the sealed end of said first chamber, whereby when the orifice in said second chamber is opened, atmospheric pressure acting upon said plunger means drives the first chamber movable wall of the plunger toward the sealed end of the first chamber and drives the portion of the plunger received by the second chamber toward the orifice of the second chamber to thereby drive the fluid contained in said second chamber through the orifice to deliver the fluid from the apparatus.

7. The apparatus of claim 6 wherein said second chamber comprises a housing for receiving a flexible container capable of carrying fluid to be delivered from said apparatus, said flexible container having collapsible walls, and being carried in said housing.

8. The apparatus of claim 6 wherein said orifice in said second chamber includes valve means.

9. The apparatus of claim 8 wherein said apparatus includes a fluid administration set in communication with said orifice for further controlling the rate of flow of fluid from said apparatus.

10. An apparatus for delivering fluid with a relatively constant, controlled rate of flow comprising, in combination, a first vacuum power chamber for driving the fluid to be delivered from the apparatus, said first chamber comprising a sealed portion comprising at least a partial vacuum, a separate second chamber adapted to receive a fluid mounted to said first chamber in axial alignment therewith, and plunger means comprising a first head, a second head and a rod for connecting said first and second heads, said first chamber having a first end open to the atmosphere, and having a second end which forms an opening for sealingly and slidingly receiving said rod of said plunger means, said second chamber having a first end capable of receiving said second head of said plunger means in sealing and sliding engagement with said second chamber, and said second chamber having a second end which forms an orifice for the delivery of fluid, said first head of said plunger means being disposed in said first chamber so that said first head forms a movable wall for said sealed portion, said first head sealingly and slidingly engaging said first chamber and said rod extending through said opening in said second end of said first chamber in sealing and sliding engagement with said opening, said rod terminating in a second head for sealing and sliding engagement with said second end of said second chamber, said first chamber being evacuated when said first head is substantially at the open end of the first chamber so that atmospheric pressure acts upon said first head to drive it towards the first end of said first chamber, whereby when said orifice is opened, atmospheric pressure acting upon said first head of said plunger means drives said first head toward the first end of said first chamber and drives said second head of said plunger means toward the orifice of the second chamber to thereby drive the fluid contained in said second chamber through the orifice to deliver the fluid.

11. The apparatus of claim 10 wherein said second chamber is detachably secured to said first chamber.

12. The apparatus of claim 10 wherein said second chamber is affixed to said first chamber.

13. The apparatus of claim 10 wherein said first head is in sealing and sliding assembly with said rod means and includes engaging means for engaging said rod means when said first head is substantially at the open end of said first chamber, and handle means secured to said first head to permit the first head to be moved toward said open end of said vacuum power chamber to allow said engaging means to engage said rod means.

14. The apparatus of claim 10 wherein said orifice in said second chamber includes valve means.

15. The apparatus of claim 10 wherein said apparatus includes a fluid administration set in communication with said orifice for further controlling the rate of flow of fluid from said apparatus.

16. An apparatus for delivering fluid with a relatively constant, controlled rate of flow comprising, in combination, a vacuum power means for driving the fluid to be delivered from the apparatus, said vacuum power means comprising a sealed portion comprising at least a partial vacuum, a receptacle means carried by said vacuum power means for receiving and carrying a fluid storage means in axial alignment with said vacuum power means, fluid storage means adapted to receive fluid and adapted to be received in and carried by said receptacle in axial alignment with said vacuum power means, and plunger means carried in said vacuum power means to effect delivery of fluid from the apparatus, said plunger means forming a movable wall of said sealed portion in sealing and sliding engagement with said vacuum power means and rod means extending from said movable wall, said vacuum power means having a first end open to the atmosphere, and having a second end which forms an opening for sealingly and slidably receiving said rod means, said plunger means being disposed in said vacuum power means so that the movable wall of said plunger means forms one end of said sealed portion of said vacuum power means, said rod means of said plunger means extending axially from said vacuum power means in axial alignment with said receptacle, said plunger means having a handle means and locking means for drawing said plunger means toward the open end of said vacuum power means and locking said plunger means substantially at the open end of said vacuum power means, the vacuum power means being evacuated when said movable wall of said plunger means is substantially at the open end of said vacuum power means so that atmospheric pressure acts upon said plunger means to drive it toward the sealed end of said vacuum power means, said fluid storage means having a first end capable of receiving said plunger means and having a second end which forms an orifice for the delivery of fluid, said plunger means being in axial communication with said fluid storage means so that when said plunger locking means is unlocked and the orifice in said fluid storage means is opened, atmospheric pressure acting upon said movable wall of said plunger means drives said movable wall toward the sealed end of said vacuum power means and drives said rod means toward the orifice of said fluid storage means to thereby drive the fluid contained in said fluid storage means through the orifice to deliver the fluid from the apparatus.

17. The apparatus of claim 16 wherein said fluid storage means comprises a flexible container capable of carrying fluid to be delivered from said apparatus, said flexible container having collapsible walls and being carried in said receptacle.

18. The apparatus of claim 16 wherein said fluid storage means includes a movable wall at said first end thereof, said movable wall being capable of receiving said rod means of the plunger means so that as the movable wall of said plunger means is driven toward the sealed end of the vacuum power means said rod means engages said movable wall of said fluid storage means and said movable wall of said fluid storage means is driven toward the orifice of said fluid storage means to thereby drive fluid contained in said fluid storage means through the orifice to deliver fluid from the apparatus.

19. The apparatus of claim 18 wherein said movable wall of said fluid storage means is in sealing and sliding engagement with said fluid storage means and forms a movable cover of said fluid storage means.

20. The apparatus of claim 19 wherein said orifice in said fluid storage means includes valve means.

21. The apparatus of claim 20 wherein said apparatus includes a fluid administration set in communication with said orifice for further controlling the rate of flow of fluid from said apparatus.

22. The apparatus of claim 16 wherein said orifice in said fluid storage means includes valve means.

23. The apparatus of claim 22 wherein said apparatus includes a fluid administration set in communication with said orifice for further controlling the rate of flow of fluid from said apparatus.

24. The apparatus of claims 5, 3, 9, 15, 23 or 21 wherein said fluid administration set includes lure means for opening said valve means, said lure means comprising a first elongated tubular section having a first diameter, and a second elongated tubular section having a second diameter, the first diameter of said first tubular section being greater than the second diameter of said second elongated tubular section, and a tapered section connecting said first elongated tubular section to said second elongated tubular section, said second elongated tubular section being sufficiently long and having a diameter such that said lure means is capable of press fitting into said valve means to form a seal between said second elongated section and said valve means prior to said valve means being opened sufficiently to permit fluid to flow therethrough.

25. The apparatus of claims 4, 8, 14, 22 or 20 wherein said valve means is a duck bill valve.

* * * * *

UNITED STATES PATENT AND TRADEMARK OFFICE
CERTIFICATE OF CORRECTION

PATENT NO. : 5,135,500
DATED : August 4, 1992
INVENTOR(S) : BRIAN D. ZDEB It is certified that error appears in the above-identified patent and that said Letters Patent is hereby corrected as shown below:

Column 2, line 13, after the word "controlled" delete "by" and substitute therefor -- to --;

Column 7, lines 55 and 56, after "orifice" add -- 20 of the fluid storage means. Second head 23a will --; and Column 8, line 7, insert before "26" -- means --.

Claim 1, Column 12, line 37, delete "forward" and substitute therefor -- toward --; and Claim 1, Column 12, line 51, after "chamber" insert -- to thereby drive the fluid contained in said second chamber --.

Signed and Sealed this

Twenty-eighth Day of September, 1993

*Attest:*

BRUCE LEHMAN

*Attesting Officer*    Commissioner of Patents and Trademarks